(12) United States Patent
Chen et al.

(10) Patent No.: US 7,049,489 B2
(45) Date of Patent: May 23, 2006

(54) GENES FOR CONTROLLING FLORAL DEVELOPMENT IN ORCHID

(75) Inventors: Hong-Hwa Chen, Tainan (TW); Wen-Chieh Tsai, Chiayi (TW); Wen-Huei Chen, Tainan (TW)

(73) Assignee: National Cheng Kung University, Taiwan (CN)

( * ) Notice: Subject to any disclaimer, the term of this patent is extended or adjusted under 35 U.S.C. 154(b) by 0 days.

(21) Appl. No.: 10/690,246

(22) Filed: Oct. 21, 2003

(65) Prior Publication Data

US 2004/0210967 A1    Oct. 21, 2004

(30) Foreign Application Priority Data

Oct. 25, 2002    (TW) ............................... 91125320 A

(51) Int. Cl.
*C12N 15/29* (2006.01)
*C12N 15/82* (2006.01)
*C12N 15/87* (2006.01)
*C12N 5/04* (2006.01)
*A01H 5/00* (2006.01)

(52) U.S. Cl. ...................... 800/290; 800/278; 800/298; 800/287; 800/293; 800/323; 536/23.1; 536/23.6; 435/320.1; 435/410; 435/419; 435/252.3

(58) Field of Classification Search ................ 800/287, 800/290, 278, 298, 293, 323; 435/6, 69.1, 435/200, 419, 468, 320.1, 410, 252.3; 536/23.6, 536/23.1

See application file for complete search history.

(56) References Cited

U.S. PATENT DOCUMENTS 6,133,435 A * 10/2000 Fernandez et al. ......... 536/23.6
6,395,892 B1 * 5/2002 Strauss et al. ............. 536/24.1

OTHER PUBLICATIONS

Guo et al., Protein Tolerance to Random Amino Acid Change, PNAS., 101:9205-9210, 2004.*
Hill et al., Functional Analysis of Conserved Histidines in ADP-Glucose Pyrophosphorylase From *Escherichia coli*, Biochemical and Biophysical Research Communications, 244:573-577, 1998 □ □ □ □.*
Lazar et al., Transforming Growth Factor: Mutation of Aspartic Acid 47 and leucine 48 Results in Different Biological Activities, Molecular and Cellular Biology, 8:1247-1252, 1988.*
Branch, A., A Good Antisense Molecule is Hard to Find. TIBS, 23:45-50, 1998.*
Kang et al., Phenotypic Alterations Of Petal and Sepal By ectopic Expression Of A Rice MADS Box Gene In Tobacco, Plant Molecular Biology, 29:1-10, 1995.*
Weigel, Detlef and Elliot M. Meyerowitz. "The ABCs of Floral Homeotic Genes." *Cell* (1994) 78: 203-209.

Theissen G. et al. "A short history of MADS-box genes in plants." *Plant Molecular Biology* (2000) 42:115-149.
TheiBen G. et al. "Classification and Phylogeny of the MADS-Box Multigene Family Suggest Defined Roles of the MADS-Box Gene Subfamilies in the Morphological Evolution of Eukaryotes." *J. Mol. Evol.* (1996) 43: 484-516.
Moon Y.-H. et al. "Identification of a rice *APETALA3* homologue by yeast two-hybrid screening." *Plant Molecular Biology* (1999) 40: 167-177.
Ambrose, B.A. et al. "Molecular and Genetic Analyses of the *Silky 1* Gene Reveal Conservation in Floral Organ Specification between Eudicots and Monocots." *Molecular Cell* (2000) 5: 569-579.
Münster, T. et al. "Characterization of three *GLOBOSA*-like MADS-box genes from maize: evidence for ancient paralogy in one class of floral homeotic B-function gene of grasses." *Gene* (2001) 262: 1-13.
Becker, A. et al. "MADS-Box Gene Diversity in Seed Plants 300 Million Years Ago." *Mol. Biol. Evol.* (2000) 17(10): 1425-1434.
O'Neill, S.D. et al. "Interorgan Regulation of Ethylene Biosynthetic Genes by Pollination." *The Plant Cell* (1993) 5: 419-432.
Altschul, S.F. et al. "Gapped BLAST and PSI-BLAST: a new generation of protein database search programs." *Nucleic Acids Research* (1997) 25(17): 3389-3402.
Purugganan, M.D. et al. "Molecular Evolution of Flower Development: Diversification of the Plant MADS-Box Regulatory Gene Family." *Genetics* (1995) 140: 345-356.
Carlson, J.E. et al. "Segregation of random amplified DNA markers in $F_1$ progeny of conifers." *Theor. Appl. Genet.* (1991) 83: 194-200.
The whorl-specific action of a petunia class B floral homeotic gene: Suguru Tsuchimoto, Tomoko Mayama, Alexander van der Krol, Eiichi Ohtsubo: Genes to Cells (2000) 5, 89-99.
Molecular and Genetic Analyses of the Silky 1 Gene Reveal Conservation in Floral Organ Specification between Eudicots and Monocots: Barbara Ambrose, David Lerner, Christopher Padilla, Martin Yanofsky, Robert Schmidt: Molecular Cell, vol. 5,569-579, Mar. 2000.
The Arabidopsis homeotic genes APETALA3 and PISTILLATA are sufficient to provide the B class organ identity function: Beth allyn Krizek, Elliot M. Meyerowitz, Development 122, 11-22 (1996).
A MADS Box Gene from Lily (lilium Longiflorum) is Sufficient to Generate Dominant Negative Mutation by Interacting with PISTILLATA (PI) in *Arabidopsis thaliana*: Tsai-Yu Tzeng andChang-Hsien Yang: Plant cell Physiol 42(10): 1156-1168 (2001).

* cited by examiner

*Primary Examiner*—Elizabeth McElwain
*Assistant Examiner*—Stuart F. Baum
(74) *Attorney, Agent, or Firm*—Ladas & Parry LLP

(57) ABSTRACT

The present invention provides PeMADS2, PeMADS3, PeMADS4 and PeMADS5 for controlling floral development in orchid. The present invention also provides a protein, a vector, a cell, a protocorn, and a kit for controlling the floral development in orchid. A method for producing transgenic orchid and a transgenic orchid are provided.

25 Claims, 10 Drawing Sheets

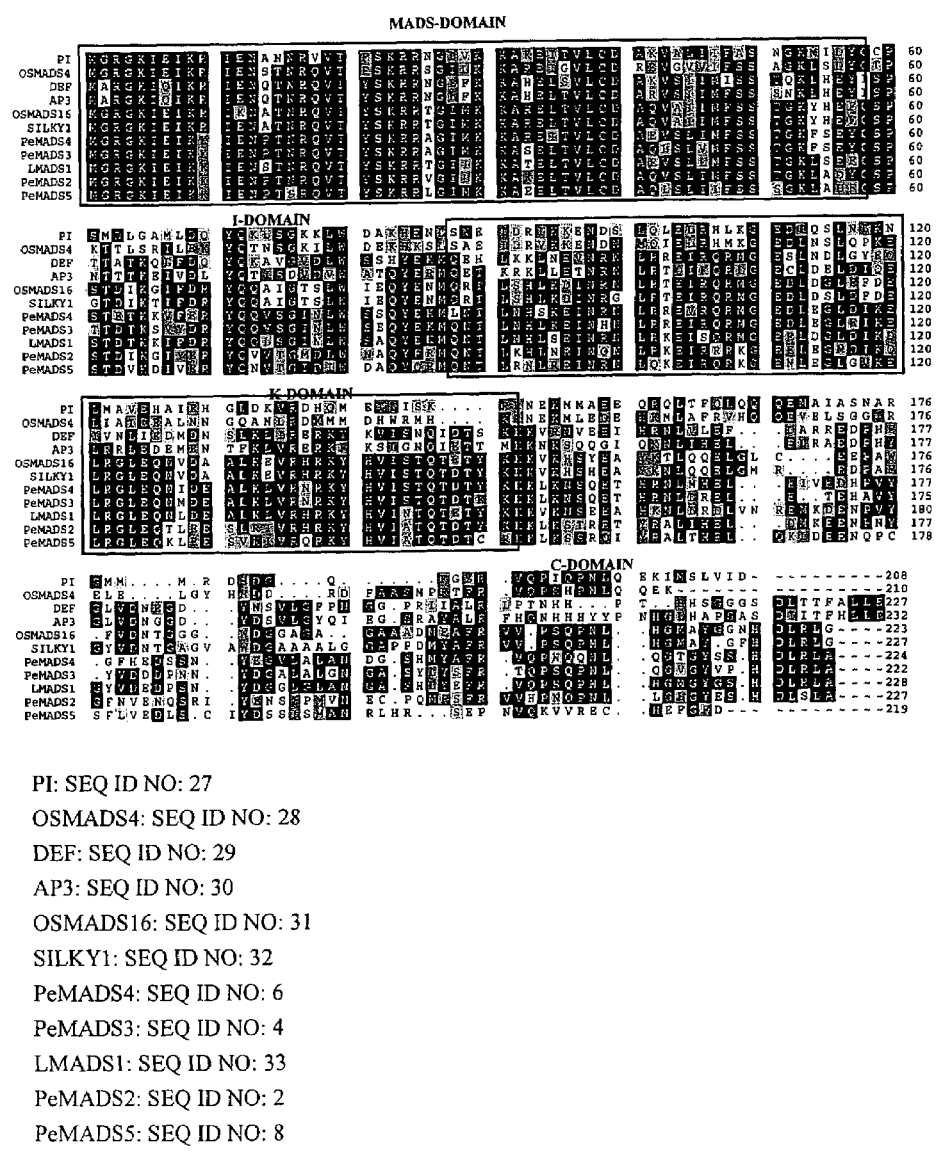

PI: SEQ ID NO: 27
OSMADS4: SEQ ID NO: 28
DEF: SEQ ID NO: 29
AP3: SEQ ID NO: 30
OSMADS16: SEQ ID NO: 31
SILKY1: SEQ ID NO: 32
PeMADS4: SEQ ID NO: 6
PeMADS3: SEQ ID NO: 4
LMADS1: SEQ ID NO: 33
PeMADS2: SEQ ID NO: 2
PeMADS5: SEQ ID NO: 8

FIG. 2

|  | PI Motif-Derived | PaleoAP3 Motif |
|---|---|---|
| DR6 (SEQ ID NO: 34) | --VHNIYAFR LQPL-HPNLQ | NE-GG-FGSR -DLRLS |
| OSMADS16 (SEQ ID NO: 35) | GAAADMFAFR VVPS-QPNLH | GMAYGGN--H -DLRLG |
| TAMADS51 (SEQ ID NO: 36) | GLAADMYAFR VVPS-QPNLH | GMAYGGS--H -DLRLG |
| SILKY1 (SEQ ID NO: 37) | GAPPDMYAFR VVPS-QPNLH | GMAYG-F--H -DLRLG |
| SmAP3 (SEQ ID NO: 38) | RPADVGYAFH HSAG-QSNVH | ---DVGYGFH -ELRLA |
| PeMADS3 (SEQ ID NO: 39) | ---SYIYSFR TQPS-QPNLQ | ---GVGYVPH -DLRLA |
| PeMADS2 (SEQ ID NO: 40) | ---PQMFSFR VVHPNQPNLI | ---GLGYESH -DLSLA |
| PeMADS4 (SEQ ID NO: 41) | ---SHHYAFR VQPN-QQNLQ | ---GTGYSSH MDLRLA |
| LMADS1 (SEQ ID NO: 42) | NGASHIYEFR VQPS-QPNLH | ---GMGYGSH -DLRLA |
| PnAP3-2 (SEQ ID NO: 43) | ---PNIFAFR LQPS-QPNLH | N--GGGYNCH -DLRLA |
| MfAP3 (SEQ ID NO: 44) | ---AHI---- --------LH | D---TGFGIH -DLRLA |
| DeAP3 (SEQ ID NO: 45) | ---QNIFAFR LQPS-QPNLH | D--GGGYGSH -DLRLA |
| PeMADS5 (SEQ ID NO: 46) | YDSSISMANR LHRS-EPNVQ | ---KVVRECH -EFGFD |
| CMB2 (SEQ ID NO: 47) | AAA-NIFALS RHPIT----- | ----------- ------ |
| Consensus (SEQ ID NO: 48) | ------F.FR LQPS.QPNLH | ------YG-H -DLRLA |

FIG. 3

| | Se | Pe | Li | Co |
|---|---|---|---|---|
*PeMADS2* 
*PeMADS3* 
*PeMADS4* 
*PeMADS5* 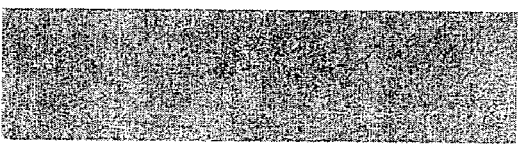
*28S rDNA* 
      6   7   8   9
FIG. 7b

GENES FOR CONTROLLING FLORAL DEVELOPMENT IN ORCHID

This application claims the benefit of priority under 35 USC 119 of Taiwan application No. 091125320, filed Oct. 25, 2002.

BACKGROUND OF THE INVENTION

1. Field of the Invention

The invention mainly relates to genes for controlling floral development in orchid. In particular, the invention relates to genes for controlling sepal, petal, lip, and stamen developments.

2. Description of the Related Art

*Phalaenopsis* spp., which has a single axis stem, is a member of *Orchidaceae* family. It is one of the most important ornamental flowers exporting from Taiwan, and has been selected for developing as a delicate agriculture industry. *Phalaenopsis* attracts people by its elegant floral morphology. The *Phalaenopsis* with special floral morphology has a high value in the market.

The flowers of general monocots or eudicots have different types of organs arranged in concentric whorls. The outermost whorl contains sepals and the next whorl contains petals. The third whorl contains the stamens. Furthermore, the female reproductive organs occupy the center of the flower. In the modern molecular biotechnology, a plant having a special floral morphology can be bred by changing the expression of genes for controlling flower development based on the understanding of the regulation mechanism of floral development. In the model plants such as *Arabidopsis* and snapdragon, the genes for controlling floral development and mechanism thereof are well studied (Weigel, D. and Meyerowitz, E. M. 1994. The ABCs of floral homeotic genes. Cell 78, 203–209). In the model plants, the flower controlling mechanism is "ABC model" in which three flower controlling genes A, B and C alone or in combination control the flower organ development. Expression of A alone specifies sepal formation. The combination of AB specifies the development of petals, and the combination of BC specifies the stamen formation. Expression of C alone determines the development of carpels (Theissen et al., 2000. A short history of MADS-box genes in plants. Plant Mol. Biol. 42, 115–149).

These genes A, B and C are all transcription factor genes and the gene products thereof have a MIKC-type domain structure comprising a MADS-box (M) domain, an intervening (I) domain, a keratin-like (K) domain, and a C-terminal (C) domain. The MADS-box domain is considered to play an important role in controlling floral development in *Arabidopsis* and snapdragon (Weigel and Meyerowitz, 1994).

All B-function genes belong to the family of MADS-box genes and fall into either one of two different clades, namely DEF— or GLO-like genes (Theissen et al., 1996, Classification and phylogeny of the MADS-box multigene family suggest defined roles of MADS-box gene subfamilies in the morphological evolution of eukaryotes. J. Mol. Evol. 43, 484–516). DEF- and GLO-like genes are closely related to the MADS-box gene family. These two clades together also represent a well supported gene lade (Theissen et al., 1996). In addition to the higher eudicots, B genes have been most intensively studied in cereal grasses (family *Poaceae*), mainly the important crop plants and rice and maize model system (Moon et al., 1999. Identification of a rice APETALA3 homologue by yeast two-hybrid screening. Plant Mol. Biol. 40, 167–177; Ambrose et al., 2000. Molecular and genetic analyses of the silkyl gene reveal conservation in floral organ specification between eudicots and monocots. Mol. Cell 5, 569–579; Münster et al., 2001. Characterization of three GLOBOSA-like MADS-box genes from maize: evidence for ancient paralogy in one class of floral homeotic B-function genes of grasses. Gene 262, 1–13). In the literature, only one DEF-like gene has been reported in diverse monocots such as lily (*Lilium regale*), wheat (*Triticum aestium*), maize and rice (Münster et al., 2001).

The orchid flower does not have the normal monocots and eudicots floral morphology. It has three sepals, three petals and one of the petals possesses a different morphological structure known as the lip. The male and female reproductive parts are combined in a uniform structure, the column, in the center of the flower. The pollen grains stick together to form pollinia located at the upper end of the column inside the anther (referring to FIG. 1a). As a reason, the result established in the model plant cannot be applied in constructing the mechanism of the elegant orchid floral morphology. In the prior art, the traditional breeding technique is still used in changing the orchid floral morphology. It spends a lot of time and the success rate is also low.

SUMMARY OF THE INVENTION

The invention provides four genes for controlling floral development in orchid after a study on the effect of the gene controlling floral development on the change of floral morphology in orchid. All of the four genes belonging to DEF-like genes have B-function of ABC model and the proteins encoded by them share a MIKC-type domain structure.

One subject of the invention is to provide an isolated nucleic acid molecule for controlling floral development in orchid, which nucleic acid molecule is selected from the group consisting of (a) a nucleic acid molecule, PeMADS2, for controlling sepal development and the anti-sense strand thereof; (b) a nucleic acid molecule, PeMADS3, for controlling lip development and the anti-sense strand thereof; (c) a nucleic acid molecule, PeMADS4, for controlling lip and column developments and the anti-sense strand thereof; (d) a nucleic acid molecule, PeMADS5, for controlling petal and stamen developments and the anti-sense strand thereof; (e) one or more nucleic acid molecules hybridizing with the complement strand of any one of the nucleic acid molecules defined in (a), (b), (c) and (d) under stringent hybridization conditions; and (f) one or more nucleic acid molecules comprising the degeneration sequence of any one of the nucleotide molecules defined in (a), (b), (c) and (d).

In another aspect, the invention provides a protein, a vector comprising the nucleic acid molecule, a cell, a protocom, and a kit for controlling the floral development in orchid.

In still another aspect, the invention provides a method for producing transgenic orchid and a transgenic orchid produced according to the method, the method comprising the steps of:

(a) introducing the nucleic acid molecule according to the invention into an orchid cell to obtain an orchid transformed cell; and (b) regenerating the orchid transformed cell to obtain the transgenic orchid plant.

In still another aspect, the invention provides a method for producing an orchid transformed cell comprising introducing the nucleic acid molecule according to the invention into an orchid cell to obtain the orchid transformed cell.

In still another aspect, the invention provides a method for controlling floral development in orchid, which comprises changing the expression of the protein according to the invention for controlling floral development.

BRIEF DESCRIPTION OF THE DRAWINGS

FIG. 2 illustrates alignment of the deduced amino acid sequences of PeMADS genes and some GLO- and DEF-like genes. The multiple alignment was generated by the computer program PILEUP and displayed by PRETTYBOX. Identity with consensus is denoted by black box. Similarity with consensus is denoted by the gray, differences are indicated by white, gaps in the alignment are indicated by points, and positions that are not occupied by an amino acid by a '~'. The MADS-, I- , K-, and C-domains are indicated. OSMADS4 and OSMADS16 are from rice; SILKY1 is from maize; LMADS1 is from lily; DEF is from Antirrhium; PI and AP3 are from Arabidopsis; PeMADS2, PeMADS3, PeMADS4, and PeMADS5 are from P. equestris.

FIG. 3 illustrates alignment of the consensus sequences for PI-derived motif and paleoAP3 motif. PeMADS2, PeMADS3, PeMADS4, and PeMADS5 are from P. equestris; OSMADS16 is from rice; SILKY1 is from maize; DR6 is from L. esculentum; TAMADS51 is from T. aestivum; SmAP3 is from S. montevidensis; PnAP3–2 is from P. nudicaule; MfAP3 is from M. figo; DeAP3 is from D. eximia; CMB2 is from D. caryophzyllus; LMADS1 is from L. iongiflorum.

DETAILED DESCRIPTION OF THE INVENTION

Figure 1A:
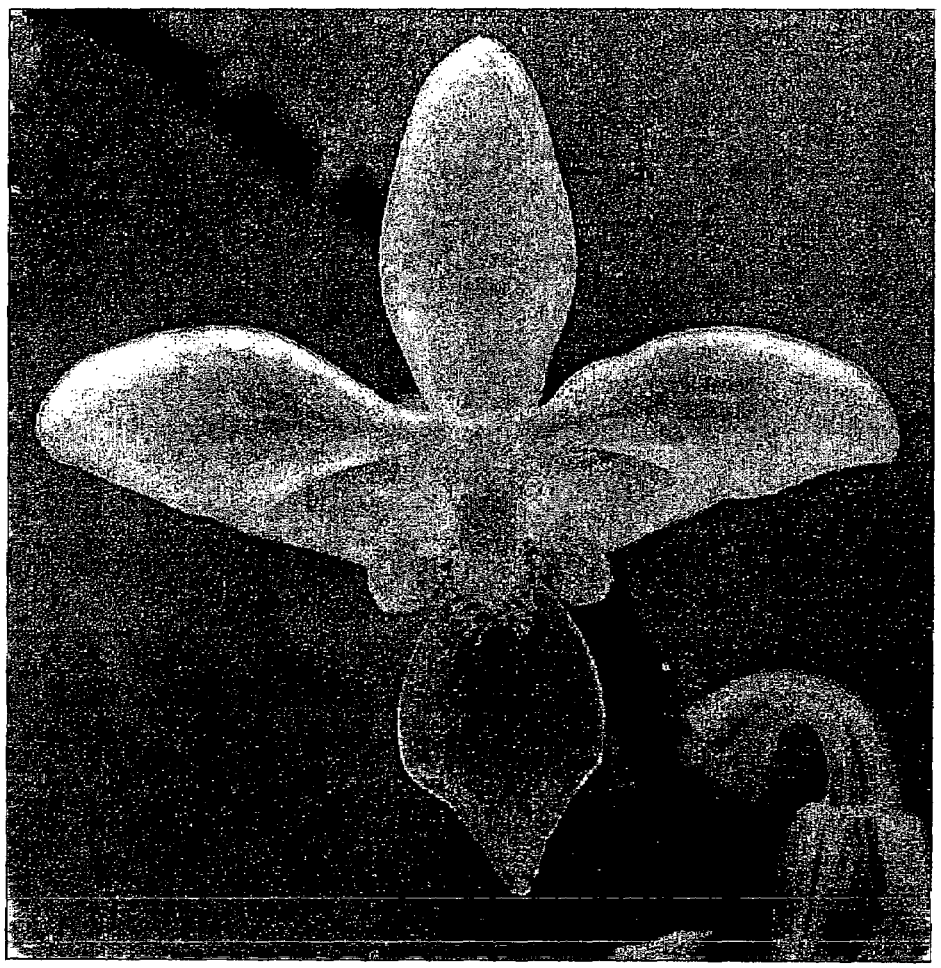
FIG. 1a illustrates the wild type flower of Phalaenopsis equestris.

The present invention mainly relates to an isolated nucleic acid molecule for controlling floral development in orchid, which nucleic acid molecule is selected form the group consisting of:

(a) a nucleic acid molecule, PeMADS2, comprising the nucleotide sequence of SEQ ID NO: 1 and the anti-sense strand thereof, (b) a nucleic acid molecule, PeMADS3, comprising the nucleotide sequence of SEQ ID NO: 3 and the anti-sense strand thereof, (c) a nucleic acid molecule, PeMADS4, comprising the nucleotide sequence of SEQ ID NO: 5 and the anti-sense strand thereof;

(d) a nucleic acid molecule, PeMADS5, comprising the nucleotide sequence of SEQ ID NO: 7 and the anti-sense strand thereof;

(e) one or more nucleic acid molecules hybridizing with the complement strand of any one of the nucleic acid molecules as defined in (a), (b), (c) and (d) under stringent hybridization conditions; and (f) one or more nucleic acid molecules comprising the degeneration sequences of any one of the nucleotide sequences of SEQ ID NO: 1, 3, 5, and 7.

According to the invention, the floral morphology of an orchid is changed if the amounts of the nucleic acid molecule and the gene product thereof are changed.

According to the invention, four expressed sequence tags (ESTs) of DEF-like genes are obtained from the cDNA clones of Phalaenopsis equestris flower buds. Four DEF-like ESTs were identified in the assembled EST database and the full-length sequences of these genes were cloned and characterized. The results showed that the P. equestris genome contains at least four different DEF-like genes, namely PeMADS2, PeMADS3, PeMADS4 and PeMADS5. The gene PeMADS2 encodes a 227-amino acid PeMADS2 protein having a sequence given in SEQ ID NO: 2. The gene PeMADS3 encodes a 222-amino acid PeMADS3 protein having a sequence given in SEQ ID NO: 4. The gene PeMADS4 encodes a 224-amino acid PeMADS4 protein having a sequence given in SEQ ID NO: 6. The gene PeMDS5 encodes a 219-amino acid PeMADS5 protein having a sequence given in SEQ ID NO: 8.

Referring to FIG. 2, the PeMADS2, PeMADS3, PeMADS4, and PeMADS5 proteins share a typical MIKC-type domain structure in multiple sequence alignments with other MADS-box proteins. The PeMADS proteins of the invention include:

(a) an MADS domain, at the amino acids 1 to 57 in the PeMADS proteins, which is highly conserved (86–96%);

(b) an intervening domain, at the amino acids 58 to 76 in the PeMADS proteins;

(c) a domain AP3 that is a highly conserved, at the amino acids 83 to 87, having a sequence (H/Q)YEXM in PeMADS2, PeMADS3 and PeMADS4, but having a sequence QYQRM in PeMADS5;

(d) a keratin-like domain, at the amino acids 77 to 151 of the PeMADS proteins;

(e) a C-terminal domain, at the amino acids 152 to the last one of PeMADS proteins.

As shown in FIG. 3, there is a PI-derived motif (FXFRLQPSQPNLH) in PeMADS2, PeMADS3 and PeMADS4 (SEQ ID NO: 25), which is of more than 60% homology and a paleoAP3 motif (YGXHDLRLA) (SEQ ID NO: 26). (Moon, Y.-H. et al., 1999. Identification of a rice APETALA3 homologue by yeast two-hybrid screening. Plant Mol. Biol. 40, 167–177.) However, PeMADS5 shows no significant similarity. Except the Pi-derived motif and paleoAP3 motif, the C-terminal domains of the PeMADS genes have a great variation, which suggests that the four PeMADS genes identified in the EST database indeed exist.

Figure 4:
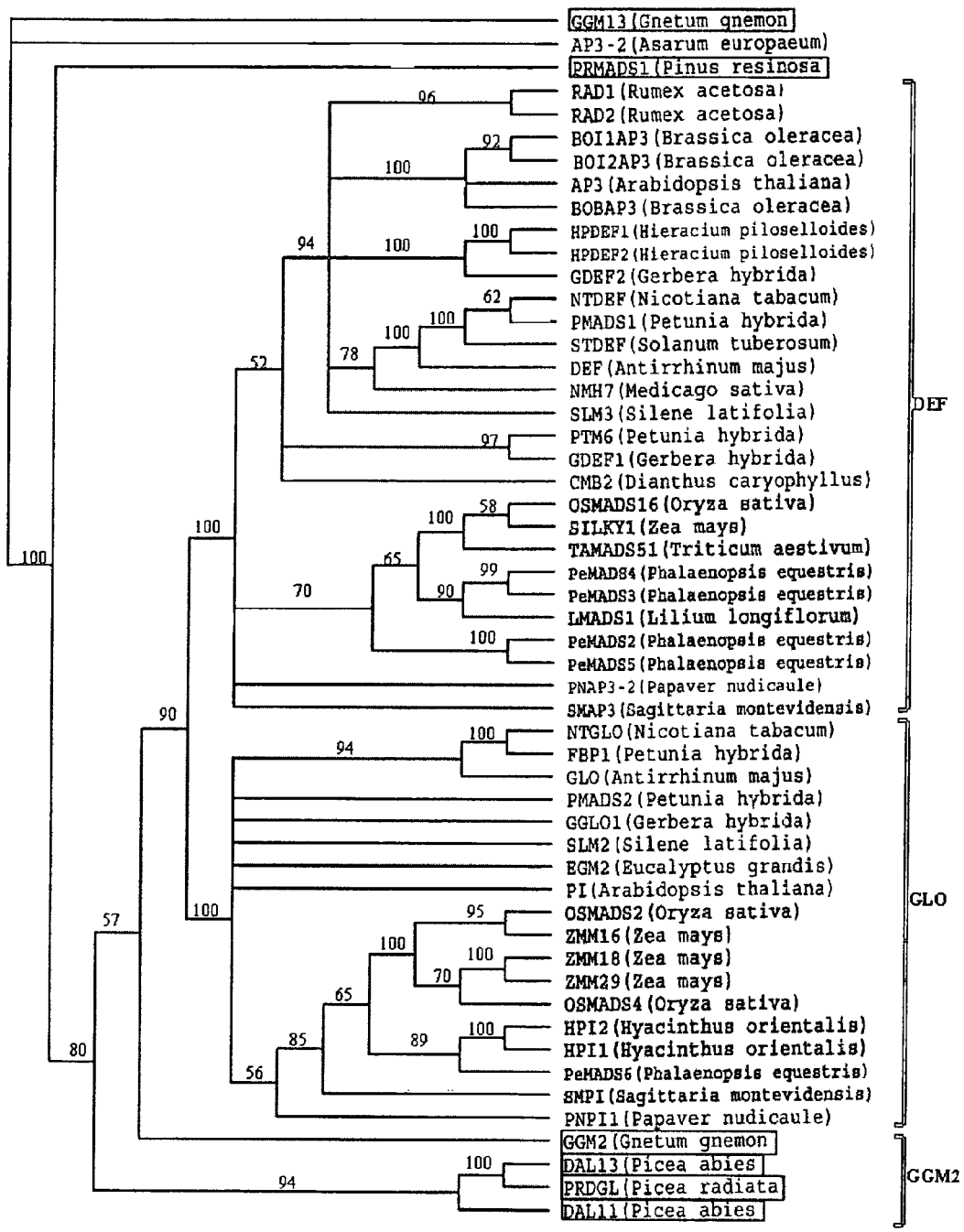
FIG. 4 illustrates phylogenetic tree of B class MADS-box genes in the DEF, GLO and GGM2 subfamilies. The phylogeny was conducted with the neighbor joining algorithm. The tree was rooted using GMM13 which is member of sister clade of the B proteins as outgroup (Becker et al., 2000. MADS-box gene diversity in seed plants 300 million years ago. Mol. Biol. Evol. 17, 1425–1434). The bootstrap values from 1000 replicates are indicated on most major nodes. Genus names of species, from which the respective genes were isolated, are given in the parentheses behind the protein names. Monocot proteins are highlighted by inverted boxes, and proteins from gymnosperms by open boxes. Proteins that are not boxed represent sequences from dicots. The monophyletic floral homeotic gene groups are marked by brackets at the right margin.
Figure 5:
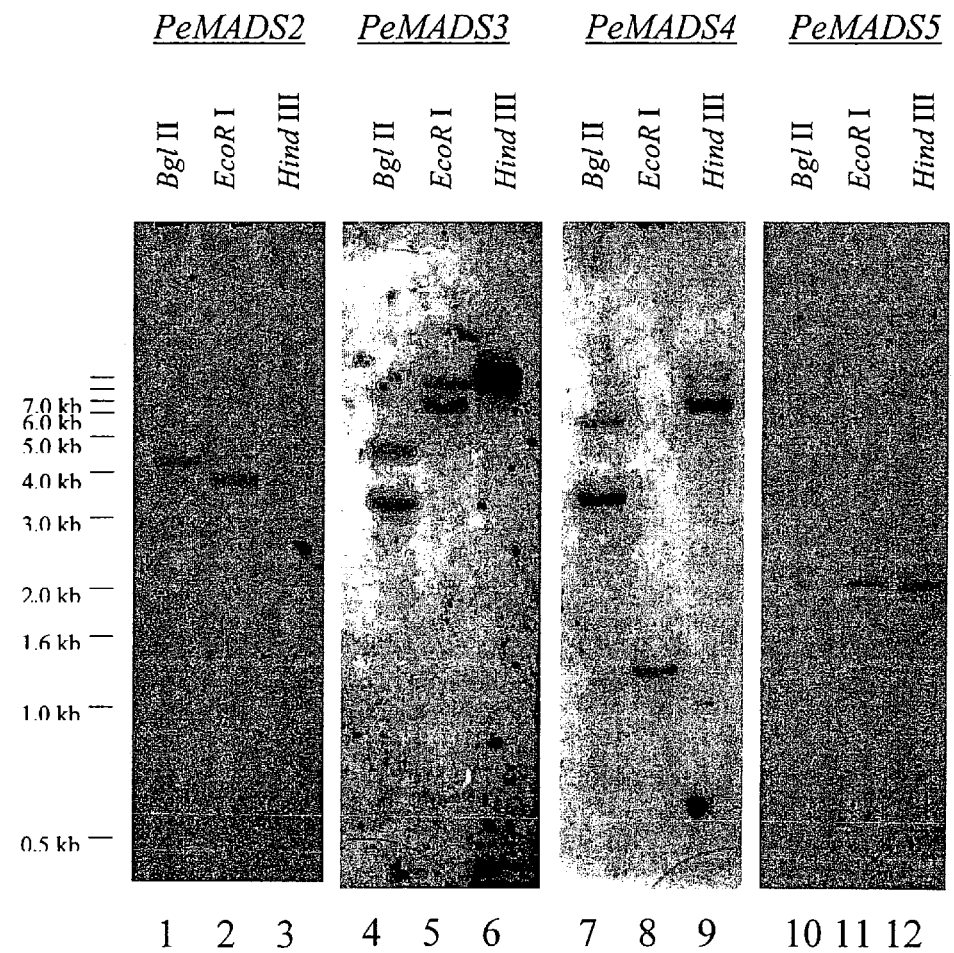
FIG. 5 illustrates Southern blot analysis of PeMADS genes in P. equestris. DNA gel blots containing 10 μg of genomic DNA digested with Bgl II (lanes 1, 4, 7, 10), Eco R I (lanes 2, 5, 8, 11), and Hind III (lanes 3, 6, 9, 12) were hybridized under stringent conditions with probes that were derived from the 3'-specific region of PeMADS genes. The names of the respective genes are indicated at the top. The lengths of DNA markers (in kb) are indicated at the left margin.

The study in topology of the phylogenetic trees having the PeMADS2, PeMADS3, PeMADS4, PeMADS5 and other MADS-box genes shows that the four genes according to the invention belong to the clade of DEF-like genes, wherein PeMADS2/PeMADS5 and PeMADS3/PeMADS4 share two common ancestors, from which they were derived by gene duplication (as shown in FIG. 4). Furthermore, a study by using a C-terminal domain as a probe shows that PeMADS2, PeMADS4, and PeMADS5 in *P. equestris* have a single copy of genes, respectively, and PeMADS3 has two copies (as shown in FIG. 5).

Figure 6:
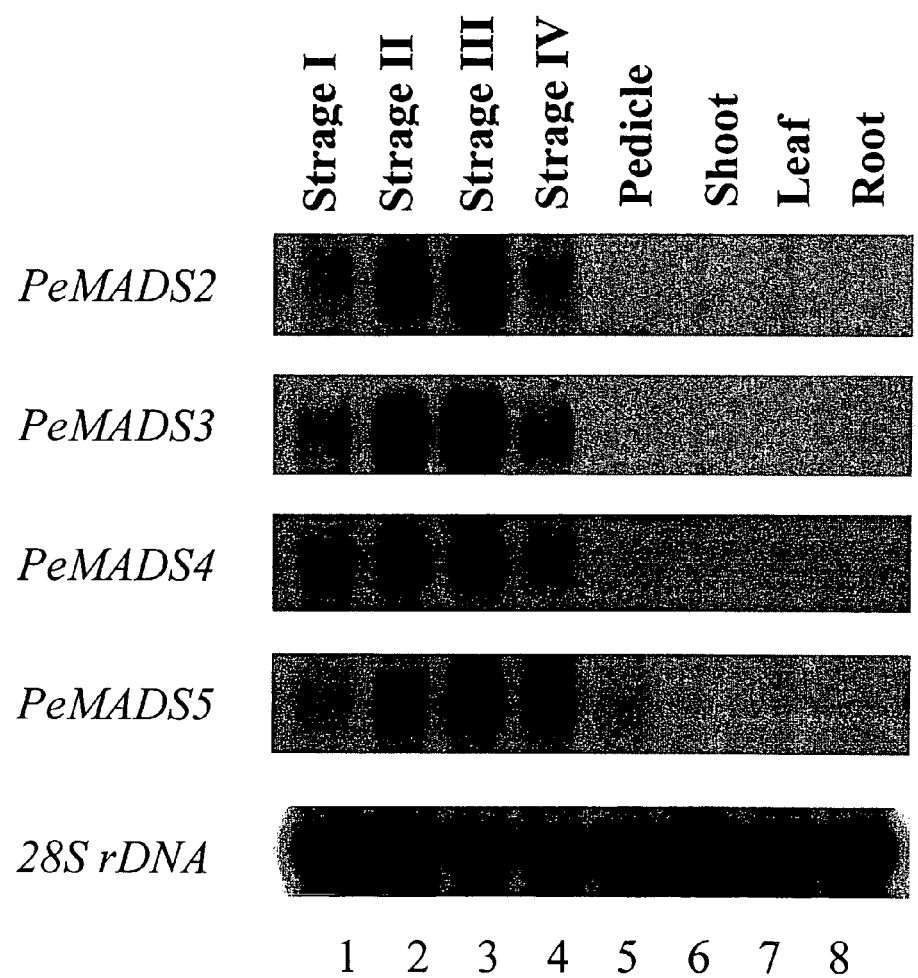
FIG. 6 illustrates expression of PeMADS genes during the development of the flower buds and in different orchid tissues. The names of the respective genes are indicated at the right margin. Each lane contained 10 μg of total RNA from: stage I to stage IV flower buds (lanes 1 to 4), pedicles (lane 5), shoots (lane 6), leaves (lane 7), and roots (lane 8). Blots were hybridized with specific probes described in "Southern blot analysis". The 28S ribosomal RNA indicated the amount of total RNA loaded in each lane.

In the floral development in orchid, four stages according to bud length are usually defined as: stage I: 0–1 mm; stage II: 1–2 mm; stage III: 2–5 mm; stage IV: 5–10 mm. The expressions of the different PeMADS genes in the buds vary at the different stages: PeMADS2, PeMADS3 and PeMADS4 genes are expressed at stages II and III, and PeMADS5 gene is expressed at stage IV (as shown in FIG. 6). Such genes are expressed in the buds from the early stage to the end of the floral development. However, the PeMADS genes are not expressed in other organs such as pedicle, shoot, leaf, or root.

The expressions of the PeMADS genes vary in different floral organs in the wild-type orchid: PeMADS2 is expressed strongly in sepal, petal and less in column, but not in lip and pollinium; PeMADS3 is expressed strongly in petal, lip and less in column, but not in sepal and pollinium; the expression of PeMADS4 is only detected in lip and column; and PeMADS5 is expressed predominantly in sepal, petal, and lip and weakly in column (referring to FIG. 7a).

Figure 1B:
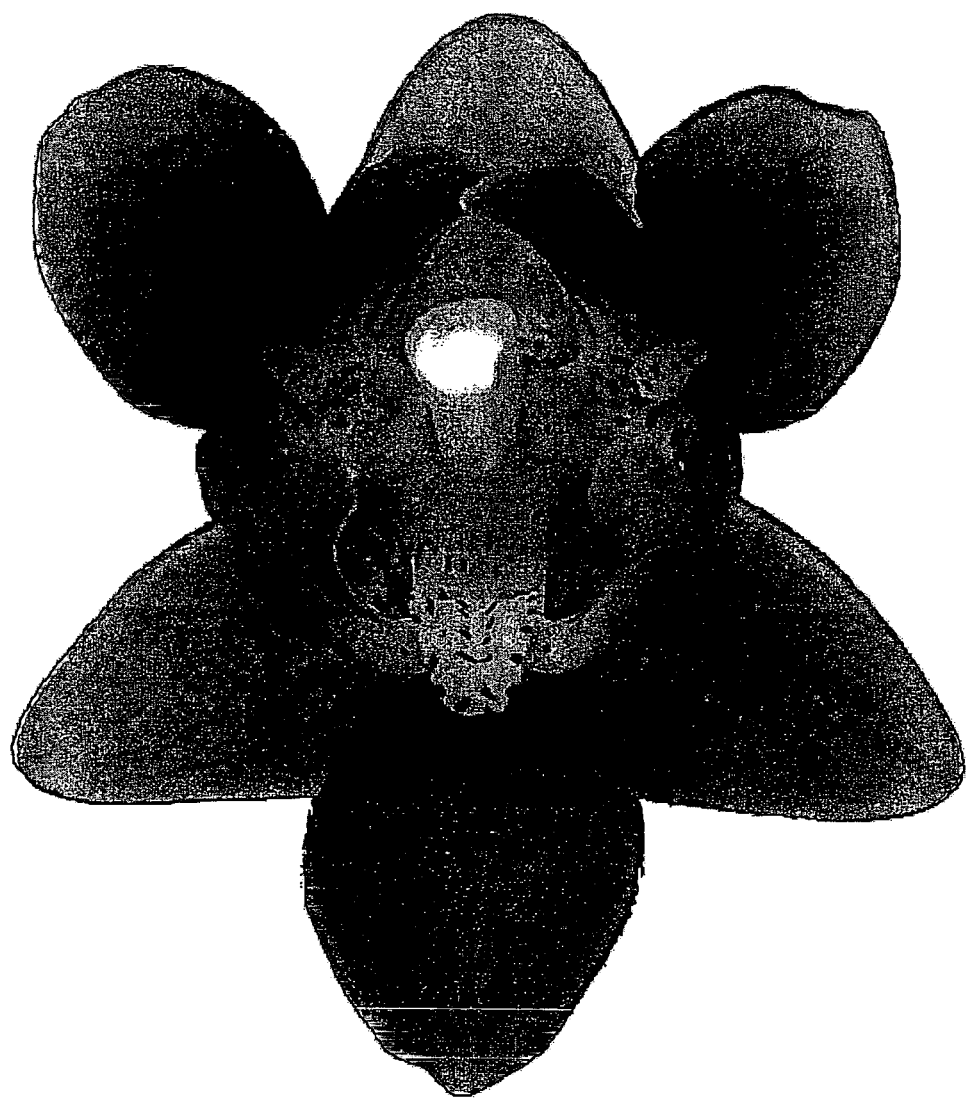
FIG. 1b illustrates the P. equistris peloric flower mutant.

The expressions of PeMADS genes of the wild-type orchid are compared with those of the mutant orchid. The mutant (referring to FIG. 1b) comprises three sepals, three lip-like petals, an arching column, a nearly reduced anther, and a flat stigma, but have no stamen primordial and pollinium. In the mutant flower, the expressions of the PeMADS genes are listed below: PeMADS2 is expressed in sepal, lip-like petal, column, and weakly expressed in lip; PeMADS3 is strongly expressed in lip-like petal, lip and column. Both of the above-mentioned genes are more strongly expressed in column of the mutant flowers than those of the wild type. PeMADS4 is strongly expressed in lip and column and weakly expressed in lip-like petal. Most strikingly, the expression of PeMADS5 was completely abolished in all floral organs of the mutant flower. These results suggest that both the positive regulation expression of PeMADS4 and the negative regulation of PeMADS5 play important roles in both petal and lip formation during the orchid floral development.

In the wild-type orchid according to the invention, PeMADS2 and PeMADS5 are strongly expressed in sepal and petal while PeMADS3 and PeMADS4 are not expressed in sepal. On the other hand, in the mutant orchid, only PeMADS2 is expressed in the sepal. In view of both the wild-type and mutant orchids both having sepal, PeMADS2 and the gene product thereof, PeMADS2, regulate sepal development. Controlling the sepal development is achieved by changing the amounts of PeMADS2 and the gene product thereof, PeMADS2, in an orchid or in an orchid cell.

In the wild-type orchid according to the invention, PeMADS3 and PeMADS4 are strongly expressed in lip while PeMADS2 and PeMADS5 are weakly expressed. On the other hand, in the mutant orchid, PeMADS4 is strongly expressed in the lip-like petal. PeMADS3 and PeMADS4 and the gene products thereof, PeMADS3 and PeMADS4, regulate lip development, and PeMADS4 and the gene product thereof, PeMADS4, possesses a different morphological structure, which is known as the lip. Controlling the lip development is achieved by changing the amounts of PeMADS4 and the gene product thereof, PeMADS4, in an orchid or in orchid cells.

In the wild-type orchid according to the invention, all PeMADS genes are not expressed in pollinium while PeMADS4 is expressed more strongly than others. It shows that PeMADS4 and the gene product thereof, PeMADS4, regulate column development. Controlling the column development is achieved by changing the amounts of PeMADS4 and the gene product thereof, PeMADS4, in orchid or in orchid cells. Furthermore, as shown in the comparison between the expression of PeMADS genes in wild-type and mutant column, PeMADS2 and PeMADS3 are expressed more strongly in the wild-type column than those in the mutant, while the expression of PeMADS5 is not detected in column. In view of the mutant lacking its stamen primordial, PeMADS5 and the gene product thereof, PeMADS5, regulate stamen primordial development. Controlling the stamen primordial development is achieved by changing the amounts of PeMADS5 and the gene product thereof, PeMADS5, in an orchid or in orchid cells.

In the wild-type orchid according to the invention, all PeMADS genes except PeMADS4 are expressed in petal. That means that PeMADS4 does not contribute in petal development. On the other hand, in the mutant orchid, PeMADS is not expressed in the petal. It is concluded that PeMADS5 and the gene product thereof, PeMADS5, regulate petal development. Controlling the petal development is achieved by changing the amounts of PeMADS5 and the gene product thereof, PeMADS5, in an orchid or in orchid cells.

As used herein, the term "anti-sense strand" refers to a nucleic acid molecule able to hybrid to the RNA transcripts of PeMADS genes under appropriate conditions. In the preferred embodiment of the invention, the anti-sense strand is a nucleic acid molecule that is complement to the RNA transcripts of the PeMADS genes. The appropriate conditions for such hybridization are the physiological or equivalent conditions found within plant cells including those found in the nucleus and cytoplasm or the standard in vitro conditions normally used by skilled persons in the art to determine sequence homology between two nucleic acids, such as at the in vitro conditions ranging from moderate (about 5×SSC at 52° C.) to high (about 0.1×SSC at 65° C.) stringency conditions.

As used herein, the term "degeneration sequence" refers to a nucleotide sequence that encodes the gene products of PeMADS genes, i.e. PeMADS proteins besides PeMADS genes.

The present invention also provides a vector for controlling floral development in orchid comprising the nucleic acid molecule according to the invention. The vector is used for storing or producing the nucleic acid molecule, or introducing the nucleic acid molecule into a plant or a plant cell. Preferably, the vector is a shuttle vector. As used herein, the term "shuttle vector" refers to a vector, which can be manipulated and selected in both a plant and a convenient cloning host, such as a prokaryote. Such a shuttle vector may include a kanamycin resistance gene for selection in plant cells and an actinomycin resistance gene for selection in a bacterial host. Besides, the shuttle vector contains an origin of replication appropriate for the prokaryotic host used, and preferably at least one unique restriction site or a polylinker containing unique restriction sites to facilitate the construction.

In another aspect, the nucleic acid molecule according to the invention is preferably driven by a promoter. More preferably, the promoter has an ability to drive expression of a nucleic acid within at least one portion of the reproductive tissues in the recipient plant, such as the cauliflower mosaic virus 35S protein promoter, the α-1 and β-1 tubulin promoter, and the histone promoters. In one embodiment of the invention, the promoter is an inducible promoter comprising but not limited to heat-shock protein promoters and light-inducible promoters including the three chlorophyll a/b light harvesting protein promoters. The methods of vector construction are well known to those skilled in the art.

The present invention also provides a kit comprising the vector according to the invention. The kit is used for controlling floral development in orchid. For convenient operation, the kit further comprises a buffer solution needed in the transformation process.

In another aspect, the invention provides a transformed cell with the vector comprising the nucleic acid molecule for controlling floral development in orchid according to the invention. The cell may be a prokaryote cell or an orchid cell, and preferably, a *Phalaenopsis* spp. cell. As used herein, the term "transformation" refers to a process for changing the genetic material of a cell through introducing a nucleic acid molecule. Persons skilled in this art can conduct the transformation according to the disclosure of the invention and normal knowledge in molecular biology. For example, the vector may be introduced into a bacterial by heat shock process, or the vector is introduced into a plant cell by a gene gun. The invention also provides a transgenic orchid comprising at least one cell transformed with the vector, which may be preformed by conventional methods known to persons skilled in the art.

The invention also provides a method for producing an orchid transformed cell comprising introducing the nucleic acid molecule into the orchid cell to obtain the orchid transformed cell.

In another aspect, the invention provides a method for producing a transgenic orchid comprising the steps of:
 (a) introducing the nucleic acid molecule according to the invention into an orchid cell to obtain an orchid transformed cell; and
 (b) regenerating the orchid transformed cell to obtain the transgenic orchid plant.

In the embodiment of the invention, a transgenic orchid plant may be produced through a protocorn-like body in vegetative planting or aspetic seed germination. The term "protocorn-like body" used herein refers to a tissue, which has a potential to differentiate and is an ability for strong and rapid proliferation ability. After separating the cells in a protocorn-like body, each can regenerate a new protocorn-like body and then a new plant. In step (a), the nucleic acid molecule is introduced into a protocorn-like body, and preferably through a gene gun. At this moment, the nucleic acid molecule is introduced into some cells in the protocorn-like body to form transformed cells, and some cells are not introduced with the molecule. The transformed cells can be selected with the marker of the vector. In step (b), the transformed cells are regenerated to transgenic plants. As used herein, the term "regeneration" refers to a growth process of a plant from a plant cell, a group of plant cells or a part of a plant. The method of regeneration is well known to persons skilled in this field. A transgenic orchid produced thereby is also provided in the invention.

In still another aspect, the invention provides a protein for controlling floral development in orchid, and preferably, *Phalaenopsis* spp. The protein is encoded by the nucleic acid molecule according to the invention. In a preferred embodiment of the invention, the protein is selected from the group consisting of PeMADS2, PeMADS3, PeMADS4, and PeMADS5, and wherein the PeMADS2, for controlling sepal development, has the amino acid sequence as given in SEQ ID NO: 2; the PeMADS3, for controlling lip development, has the amino acid sequence as given in SEQ ID NO: 4; the PeMADS4, for controlling lip and column developments, has the amino acid sequence as given in SEQ ID NO: 6; the PeMADS5, for controlling petal and stamen developments, has the amino acid sequence as given in SEQ ID NO: 8.

The invention also provides a method for controlling floral development in orchid, which comprises changing the expression of the proteins for controlling floral development in orchid. According to the invention, the method of changing the expression of the proteins comprises the steps of inducing, inhibiting and deleting the expression. In one embodiment of the invention, the expression of the proteins can be changed by increasing or decreasing the ploid of the nucleic acid molecule encoding the proteins in at least one cell of the plant. In a preferred embodiment of the invention, a gene gun is used to introduce the nucleic acid molecule into the cell for changing the expression of the protein. In another embodiment of the invention, the expression of the proteins can be changed by introducing an anti-sense strand of the nucleic acid molecule into the cell. In one embodiment of the invention, the cell is derived from a protocorn-like body.

As used herein, the phrase "changing floral morphology" refers to a physical modification in the structure of a plant's reproductive tissue as compared to the parent plant. In an embodiment of the invention, a transgenic plant can be obtained by regenerating a transformed plant cell with the genes of the invention that are capable of modifying the phenotype of the plant, wherein the cells of the transgenic plant all have the same genetic material. In another embodiment of the invention, a mosaic plant can be obtained by transforming some of cells in a plant, such as reproductive cells or tissues, with the genes of the invention, wherein only the transformed cells express the modified phenotype as compared to the parent plant.

According to the invention, the plants to be transformed with the genes include orchid and orchid cells, preferably

*Phalaenopsis* spp., which may be the wild type and an artificial mutant that produced by such as chemical modification, X-ray activated random mutagenesis or recombinant techniques.

The following Examples are given for the purpose of illustration only and are not intended to limit the scope of the present invention.

EXAMPLE

Plant materials and RNA preparation: The wild type *P. equestris* having red sepals and orange petals (referring to FIG. 1*a*) and its peloric mutant having lip-like petals, an arching column, a nearly reduced anther, a flat stigma and no stamen primordial and pollinium (referring to FIG. 1*b*) were grown in the greenhouses at Taiwan Sugar Research Institute (TSR1) with natural light and controlled temperatures ranged from 23° C. to 27° C.

Figure 1C:
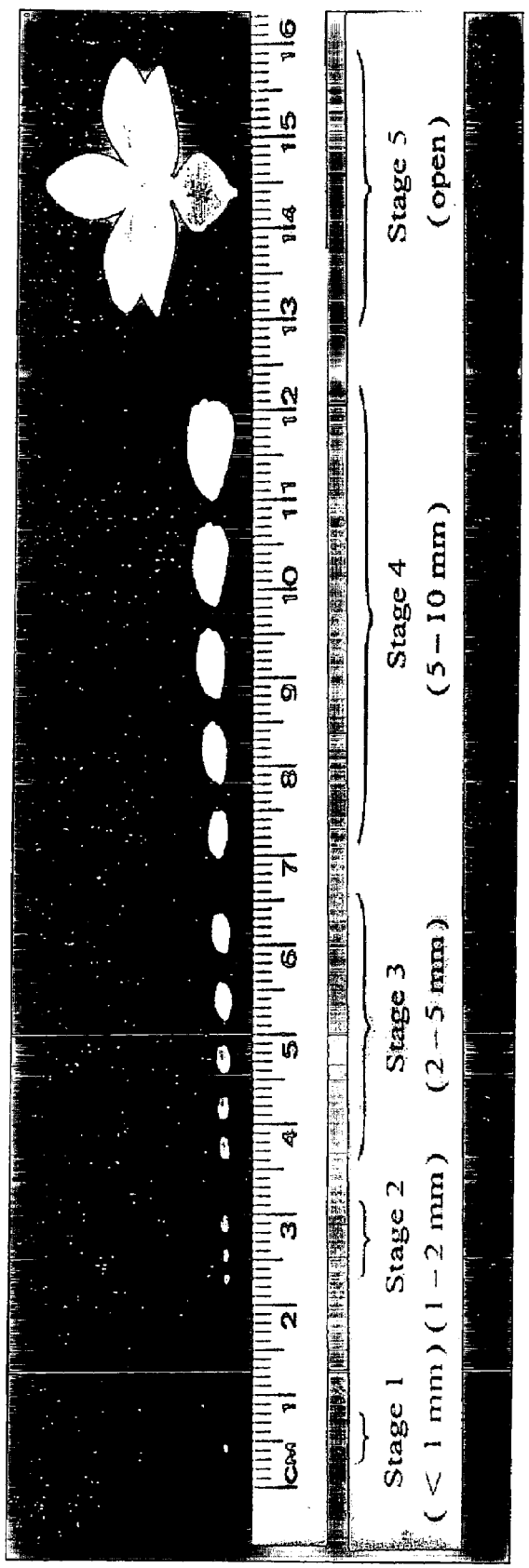
FIG. 1c illustrates the developmental stages of flower buds.

For RNA extraction, roots, leaves, shoots, developing flower buds from stages I–IV (referring to FIG. 1*c*), and various organs of flower buds including sepals, petals, lips, pollinium, and columns of developing flowers (stage IV) were collected, immersed in liquid nitrogen, and stored at −80° C. until used for RNA extraction. Total RNA was extracted following the method described by O'Neill et al. (O'Neill, S. D. et al. 1993. Interorgan regulation of ethylene biosynthetic genes by pollination. Plant Cell 5, 419–32.)

cDNA library construction: Poly (A)$^+$ mRNA was prepared from stage IV flower buds of *P. equestris* using Poly (A) Quick RNA Isolation kit (Stratagene®, La Jolla, Calif.). The synthesis of cDNA, size selection, addition of linkers, insertional ligation, and packaging into λ vector were carried out following the manufacture's instructions (λZAPII, Strategene®). The total primary titer of cDNA library was $1.1 \times 10^6$ pfu/ml. The phage library was converted to the plasmid form by mass excision according to the manufacture's protocol (Strategene®). The resulting phagimid library was plated at low density on Luria Bertani agar (LBA) plates containing kanamycin (25 mg/L). Over 4,000 randomly selected bacterial colonies from cDNA library were cultured for plasmid isolation, nucleotide sequencing and long-term storage in microtiter plates.

Plasmid DNA was purified from E. coli cultures by alkaline lysis following standard protocol, vacuum filtration, and anion-exchange chromatography using high-throughput, 96-well format system (Qiagen®, Ontario, Canada). The sequencing processes were performed by using the standard T3 sequencing primer. The sequence to the presumed 5' end of each cDNA was determined. Automated cycle sequencing of DNA was carried out using dye-labeled terminators, and the products were resolved by electrophoresis through acrylamide gels (ABI 377, Applied Biosystems ®, Foster City, Calif.).

Sequence data analysis: Raw DNA sequence data were edited to remove vector sequences, polyA sequences and poor quality data using a computer program (Sequencher 4.1, GeneCode®, Ann Arbor, Mich.). Computer-processed sequences were checked manually, compared with electropherograms, and further edited, if necessary to improve the quality and reliability of the data. Each edited EST was translated in all six reading frames and compared with the non-redundant database at the National Center of Biotechnology Information (NCBI) using the BLASTX program (Altschul et al., 1997. Gapped BLAST and PSI-BLAST: a new generation of protein database search programs. Nucleic Acids Res. 25, 3389–3402). Default BLAST parameter values were used. The sequences that had no significant similarity were further compared by BLASTN (Altschul et al., 1997).

5' rapid amplification of PeMADS cDNA ends: Rapid amplification of cDNA ends (RACE) was carried out to obtain the full-length cDNA by extending the 5' ends of cDNA using the SMART RACE cDNA amplification kit (Clontech®, Palo Alto, Calif.). In the amplification, the first strand of the cDNAs for 5' RACE was obtained from 400 ng total RNA of stage IV flower buds, the cDNA containing the 5' end for PeMADS clones were obtained by the PCR amplification using 5'-specific universal primer (Clontech®) and 3' gene-specific primer for different PeMADS genes. The gene specific primers for PeMADS2, PeMADS3, PeMADS4, and PeMADS5 are 5'-TCT CTC TGA ATA GAT CC C CCA TCT C-3' (SEQ ID NO: 9), 5'-GCA GTG CTA GAC CCT ACT TGT AAG C-3' (SEQ ID NO: 10), 5'-GCT ATA TCC CGT TCC TTG AAG ATT TTG-3' (SEQ ID NO: 11), and 5'-TCC TAT GAT GTT AAG CCA TGA AAA C-3' (SEQ ID NO: 12), respectively. The thermal cycling protocol consisted of an initial denaturation at 94° C. for 5 sec., followed by 25 cycles at 94° C. for 30 sec., 65° C. for 30 sec. and 72° C. for 2 min. and a final extension at 72° C. for 5 mm. RACE-products were re-amplified with the PeMADS nested gene-specific primers and the nested universal primer provided in the RACE kit. The nested gene-specific primers for PeMADS2, PeMADS3, PeMADS4, and PeMADS5 are 5'-TGA TTC GGA TGA ACA ACC CTA-3' (SEQ ID NO: 13), 5'-AGG AAG CCC CAT TTC CAA GTG-3' (SEQ ID NO: 14), 5'-GTG CAT TAA GTT CCG GTG TGT-3' (SEQ ID NO: 15), and 5'-TGC ACA TTT GGC TCA CTC CGG-3' (SEQ ID NO: 16), respectively. The PCR protocol consisted of an initial denaturation at 94° C. for 5 min. followed by 30 cycles at 94° C. for 30 sec., 60° C. for 2 min., 72° C. for 2 min. and a final extension at 72° C. for 5 min. The PCR products were cloned into pGEM-T Easy vector (Promega®, Madison, Wis.) and sequenced on both strands from ten positive clones.

Sequence alignments and construction of phylogenetic trees: Pairwise alignments of conceptual amino acid sequences were generated using the GAP program of the GCG package (Wisconsin Package Version 10.3, Accelrys Inc®., San Diego, Calif.) with a gap weight of 8 and a gap length weight of 2 (default parameters). Multiple alignments were generated using the PILEUP program (Wisconsin Package Version 10.3) of the same package with the same alignment parameters. The results are shown in FIGS. 2 and 3. Table 1 provides the percentage of amino acid identity and similarity at MADS-domain and the full-length sequence of DEF-like proteins from Arabidopsis, rice, maize, lily, and orchid.

TABLE 1

|  | AP3 | OSMADS16 | SILKY1 | LMADS1 | PeMADS2 | PeMADS3 | PeMADS4 | PeMADS5 |
|---|---|---|---|---|---|---|---|---|
| AP3 | — | 75.0[a]/48.9[b] | 76.7/51.1 | 73.3/51.8 | 75.0/48.2 | 71.7/48.6 | 73.3/49.1 | 70.0/47.7 |
| OSMADS16 | 80.0[c]/55.7[d] | — | 98.3/90.5 | 81.7/69.8 | 80.0/60.8 | 80.0/65.2 | 81.7/63.5 | 76.7/54.4 |

TABLE 1-continued

|  | AP3 | OSMADS16 | SILKY1 | LMADS1 | PeMADS2 | PeMADS3 | PeMADS4 | PeMADS5 |
|---|---|---|---|---|---|---|---|---|
| SILKY1 | 81.7/58.0 | 98.3/93.7 | — | 93.3/69.6 | 81.7/60.3 | 81.7/66.7 | 83.3/65.0 | 78.3/51.1 |
| LMADS1 | 83.3/61.4 | 88.3/76.6 | 90.0/75.4 | — | 85.0/66.2 | 85.0/78.0 | 86.7/76.3 | 80.0/58.3 |
| PeMADS2 | 83.3/60.5 | 90.0/71.2 | 91.7/71.4 | 93.3/78.2 | — | 86.7/64.0 | 86.7/67.0 | 86.7/68.3 |
| PeMADS3 | 80.0/57.8 | 88.3/73.3 | 90.0/73.9 | 88.3/85.6 | 91.7/75.2 | — | 91.7/80.6 | 83.3/60.3 |
| PeMADS4 | 81.7/60.5 | 91.7/73.9 | 93.3/74.0 | 91.7/86.2 | 95.0/78.1 | 96.7/87.4 | — | 80.0/58.3 |
| PeMADS5 | 80.0/61.2 | 81.7/63.7 | 83.3/60.3 | 85.0/69.3 | 90.0/75.7 | 88.3/71.5 | 86.7/69.4 | — |

[a]percentage of amino acid identity at MADS-domain of DEF-like proteins
[b]percentage of amino acid identity of the full-length sequence of DEF-like proteins
[c]percentage of amino acid similarity at MADS-domain of DEF-like proteins
[d]percentage of amino acid similarity of the full-length sequence of DEF-like proteins The result evidenced that all PeMADS proteins have specific MIKC-type domain, and PeMADS genes are MADS of DEF-like genes.

The sequences used for phylogenetic analysis includes the MADS-box domain plus the 110 amino acid downstream from the MADS-box domain (Purugganan et al., 1995. Molecular evolution of flower development: diversification of the plant MADS-box regulatory gene family. Genetics 140, 345–356). Phylogenetic trees were constructed by the neighbor-joining method and evaluated by bootstrap analysis as described (Munster et al., 1997). The result is shown in FIG. 4. It demonstrates that all the four proteins belong to B class genes from monocots, and wherein PeMADS2/PeMADS5 and PeMADS3/PeMADS4 share a common ancestor from which they were derived by gene duplication.

Isolation of genomic DNA and Southern blot analysis: Genomic DNAs were isolated from leaves following the method described by Carlson et al. (1991) (Carlson, L. E. et al. 1991. Segregation of random amplified DNA markers in F1 progeny of conifers. Theor. Appl. Genet. 83, 194–200). Genomic DNA samples were digested with restriction enzymes Bgl II, Eco R I and Hind III, resolved in 0.8% agarose gels, and transferred to nylon filters (Amersham Pharmacia Biotech®, Piscataway, N.J.) using a vacuum transfer system (Amersham Pharmacia Biotech®). The conserved MADS domain and most of K domain were excluded in the probes to avoid cross hybridization. The PeMADS2-specific probe (295 bp) was generated by PCR with PeMADS2-specific internal primer pair 5'-GAA ACT TAC CGC GCT CTA-3' (SEQ ID NO: 17) and 5'-TCT CTC TGA ATA GAT CCC CCA TCT C-3' (SEQ ID NO: 18). The PeMADS3-specific probe (284 bp) was amplified with PeMADS3-specific internal primer pair 5'-CTC TCA AGA AAC CCA CAG-3' (SEQ ID NO: 19) and 5'-GCA GTG CTA GAC CCT ACT TGT AAG C-3' (SEQ ID NO: 20). The PeMADS4-specific probe (296 bp) was amplified by using PeMADS4-specific internal primer pair 5'-GAG GAC CAC CCA GTG TAT-3' (SEQ ID NO: 21) and 5'-CAC AGA ATC ACA CAT AGC A-3' (SEQ ID NO: 22). The PeMADS5-specific probe (289 bp) was amplified by using PeMADS5-specific internal primer pair 5'-CAA ACA GAC ACT TGC AGG-3' (SEQ ID NO: 23) and 5'-TCC TAT GAT GTT AAG CCA TGA AAA C-3' (SEQ ID NO: 24). In Southern blots, the $^{32}$P-labeled probes was used for hybridization, and the pre-hybridization and hybridization were performed following the standard protocols. The result is shown in FIG. 5. It is evidenced that PeMADS2, PeMADS4 and PeMADS5 have a single copy and PeMADS3 has two copies.

RNA blot analysis: For Northern blot hybridization, Ranks were prepared from various organs of *P. equestris* plants, including stages I to IV flower buds, pedicles, shoots, leaves and roots. Total RNA samples from various floral organs, including sepal, petal, lip, pollinium and column, were prepared. Ten μg of total RNA samples were denatured with glyoxalin, subjected to electrophoresis on a 1% agarose gel, and transferred to nylon filters (Amersham Pharmacia Biotech®). The RNA blots were hybridized with the same probes as described above. The pre-hybridization and hybridization were performed following the standard protocols. For internal control, a partial fragment of 45S rDNA was used as the probe (a gift from Dr. Y. Y. Kao, Department of Botany, National Taiwan University), and the 28S rRNA band was detected.

Figure 7A:
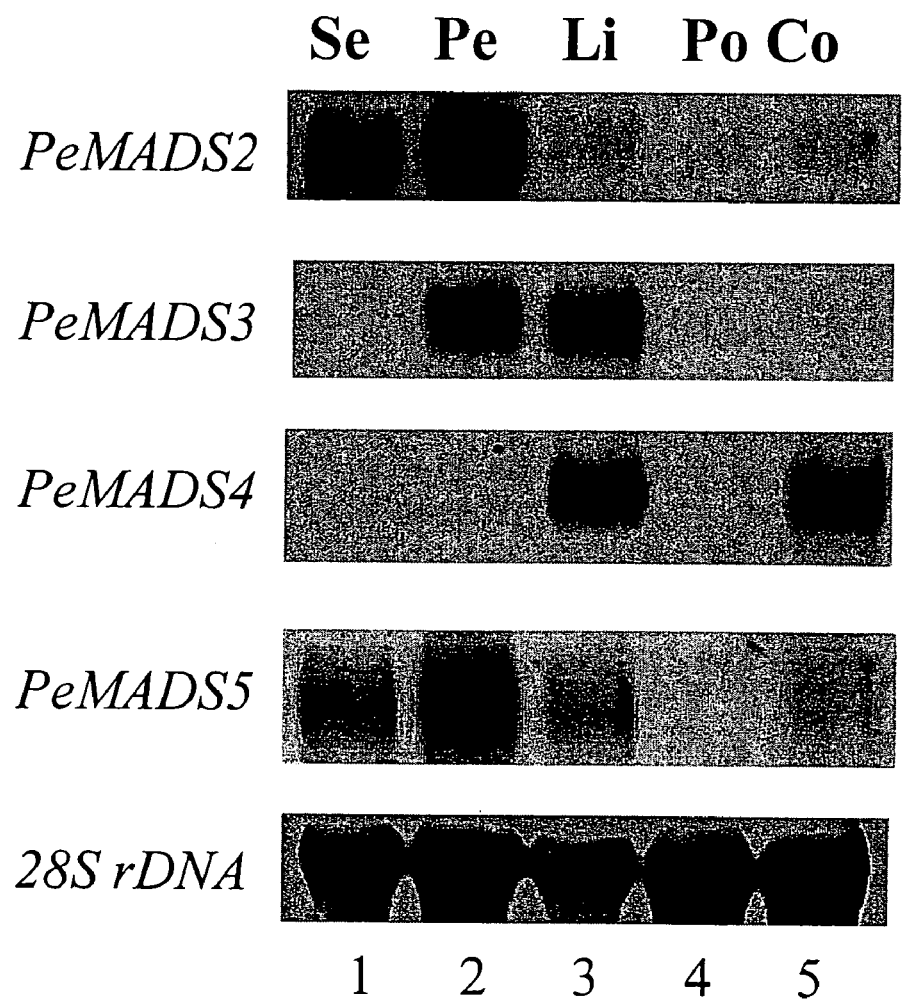
FIG. 7 illustrates Northern blot analysis of PeMADS genes in different floral organs of wild-type (FIG. 7a) and peloric mutant (FIG. 7b). RNA sources were sepals (Se) (lanes 1 and 6), petals (Pe) (lanes 2 and 7), lips (Li) (lanes 3 and 8), pollinium (Po) (lane 4), and Column (Co) (lanes 5 and 9) as indicated. The names of the respective genes are indicated at the right margin. The blot contained 10 μg of total RNA extracted from different mature floral organs in each lane. Blots were hybridized with specific probes described in "Southern blot analysis". The 28S ribosomal RNA indicated the amount of total RNA loaded in each lane.

The results of the PeMADS gene expression in different stages of flower bud development and in different orchid tissues are shown in FIG. 6. PeMADS2, PeMADS3 and PeMADS4 expressed in stage II and III, and PeMADS5 expressed in stage IV. It is evidenced that these genes express from early stage to the end of flower bud development. On the other hand, these PeMADS genes did not express in other plant tissues such as pedicles, shoots, leaves, and roots. The results of Northern blot of PeMADS genes in different tissues of the wild type and mutant are shown in FIGS. 7a and 7b. In the wild type, PeMADS2 was expressed strongly in sepal, petal and less extent in column, but not in lip and pollinium; PeMADS3 was expressed strongly in petal, lip and less in column, but not in sepal and pollinium; the expression of PeMADS4 was detected in lip and column only; and PeMADS5 was expressed predominantly in sepal, petal, and lip and weakly expressed in column. In the mutant, PeMADS2 was expressed in sepal, lip-like petal, column, and weakly in lip; PeMADS3 was expressed strongly in lip-like petal, lip and column. Both of the genes had stronger expressions in column of the mutant flowers than the wild type. PeMADS4 was expressed strongly in lip and column and weakly in lip-like petal, and the expression of PeMADS5 was completely abolished in all floral organs of the mutant flower.

While embodiments of the present invention have been illustrated and described, various modifications and improvements can be made by persons skilled in the art. The present invention is not limited to the particular forms as illustrated, and that all the modifications not departing from the spirit and scope of the present invention are within the scope as defined in the appended claims.

What is claimed is:

1. An isolated nucleic acid molecule that affects floral development in orchid, which nucleic acid molecule is selected from the group consisting of:
   (a) a nucleic acid molecule, PeMADS2, comprising the nucleotide sequence of SEQ ID NO:1; and
   (b) a nucleic acid molecule comprising degenerate sequence of SEQ ID NO:1 which encodes the PeMADS protein of SEQ ID NO:2.

2. A vector comprising the nucleic acid molecule according to claim 1.

3. The vector according to claim 2, which is a shuttle vector that is capable of expressing the nucleic acid molecule in a plant.

4. The vector according to claim 2 comprising an inducible promoter.

5. A kit for controlling floral development in orchid, which comprises the vector according to claim 2.

6. An isolated cell transformed with the vector according to claim 2.

7. A transgenic orchid comprising cells which contain the nucleic acid molecule according to claim 1.

8. A transgenic orchid produced by transforming an orchid with the vector of claim 2.

9. The cell according to claim 6, wherein the cell is a prokaryote cell.

10. The cell according to claim 6, wherein the cell is an orchid cell.

11. The cell according to claim 6, wherein the cell is a *Phalaenopsis* spp. cell.

12. A method for producing a transformed orchid cell comprising introducing the nucleic acid molecule according to claim 1 into an orchid cell to obtain the orchid transformed cell.

13. The method according to claim 12, wherein the orchid is a *Phalaenopsis* spp.

14. The method according to claim 12, wherein the orchid cell is derived from a protocom-like body.

15. The method according to claim 12, wherein introducing the nucleic acid molecule into the orchid cell is by a gene gun.

16. A protocorn-like body comprising a vector comprising the nucleic acid molecule according to claim 1.

17. A method for producing a transgenic orchid comprising the steps of:
   (a) introducing the nucleic acid molecule according to claim 1 into an orchid cell to obtain an orchid transformed cell; and
   (b) regenerating the orchid transformed cell to obtain the transgenic orchid plant.

18. The method according to claim 17, wherein the orchid plant is a *Phalaenopsis* spp.

19. The method according to claim 17, wherein the orchid cell is derived from a protocorn-like body.

20. The method according to claim 17, wherein the nucleic acid molecule is introduced into the orchid cell in step (a) by a gene gun.

21. A transgenic orchid produced according to the method according to claim 17.

22. A method for controlling floral development in orchid, which comprises transforming an orchid plant with a nucleic acid molecule according to claim 1, said nucleic acid molecule encoding a protein that is expressed in said plant.

23. The method according to claim 22, wherein a gene gun is used to introduce the nucleic acid molecule into the cell.

24. The method according to claim 23, wherein the cell is derived from a protocom-like body.

25. The isolated nucleic acid molecule according to claim 1, which consists of the nucleotide sequence of SEQ ID NO:1.

* * * * *

SEQUENCE LISTING

<160> NUMBER OF SEQ ID NOS: 24

<210> SEQ ID NO 1
<211> LENGTH: 917
<212> TYPE: DNA
<213> ORGANISM: Phalaenopsis equestris
<220> FEATURE:
<221> NAME/KEY: CDS
<222> LOCATION: (76)..(759)

<400> SEQUENCE: 1

```
acgcgggata gtagaggaag aagaagagaa gggttgagaa cagaggaaaa caggggagaa        60
caggggaaga gagag atg ggg agg ggg aag ata gag ata aaa aag ata gag       111
              Met Gly Arg Gly Lys Ile Glu Ile Lys Lys Ile Glu
                1               5                  10 aat ccg acg aac agg caa gtt aca tat tct aag agg aga gtt ggg ata        159
Asn Pro Thr Asn Arg Gln Val Thr Tyr Ser Lys Arg Arg Val Gly Ile
         15                  20                  25 ctg aag aag gcc aag gag ctc act gtt ctc tgt gat gct cag gtc tct        207
Leu Lys Lys Ala Lys Glu Leu Thr Val Leu Cys Asp Ala Gln Val Ser
 30                  35                  40 ctc atc atg ttc tca agc aca gga aag ttg gct gat tac tgc agc ccc        255
Leu Ile Met Phe Ser Ser Thr Gly Lys Leu Ala Asp Tyr Cys Ser Pro
45                  50                  55                  60 tct act gat att aag ggg ata tat gag agg tac cag gtt gtg act gga        303
Ser Thr Asp Ile Lys Gly Ile Tyr Glu Arg Tyr Gln Val Val Thr Gly
                 65                  70                  75 atg gat cta tgg aat gct cag tat gag agg atg cag aat acg ctg aag        351
Met Asp Leu Trp Asn Ala Gln Tyr Glu Arg Met Gln Asn Thr Leu Lys
             80                  85                  90 cat ctg aat gag att aac caa aac ctg agg aag gag att agg agg agg        399
His Leu Asn Glu Ile Asn Gln Asn Leu Arg Lys Glu Ile Arg Arg Arg
         95                 100                 105 aag ggg gag gaa ttg gag ggc atg gac ata aag caa ctg cgc ggt ctt        447
Lys Gly Glu Glu Leu Glu Gly Met Asp Ile Lys Gln Leu Arg Gly Leu
     110                 115                 120 gag caa act ttg gaa gag tct ctt aga att gtt agg cat aga aag tat        495
Glu Gln Thr Leu Glu Glu Ser Leu Arg Ile Val Arg His Arg Lys Tyr
125                 130                 135                 140 cat gtg atc gcc aca caa act gac act tac aag aaa aag ctt aaa agc        543
His Val Ile Ala Thr Gln Thr Asp Thr Tyr Lys Lys Lys Leu Lys Ser
                145                 150                 155 aca agg gaa act tac cgc gct cta ata cat gaa ctg gat atg aaa gag        591
Thr Arg Glu Thr Tyr Arg Ala Leu Ile His Glu Leu Asp Met Lys Glu
            160                 165                 170 gag aat ccg aac tac ggt ttt aat gta gaa aac cag agt aga att tat        639
Glu Asn Pro Asn Tyr Gly Phe Asn Val Glu Asn Gln Ser Arg Ile Tyr
        175                 180                 185 gaa aat tcg att cca atg gtg aat gag tgt cct cag atg ttt tcc ttt        687
Glu Asn Ser Ile Pro Met Val Asn Glu Cys Pro Gln Met Phe Ser Phe
    190                 195                 200 agg gtt gtt cat ccg aat cag ccc aat ctg ctt ggt tta ggt tat gaa        735
Arg Val Val His Pro Asn Gln Pro Asn Leu Leu Gly Leu Gly Tyr Glu
205                 210                 215                 220 tca cat gat ctt agc ctt gca taa tgagcagtaa tattatgatt ttattgtatt       789
Ser His Asp Leu Ser Leu Ala
                225
```

```
tttattttat gtttgaaact ttagaattat gagatggggg atctattcag agagaactgt    849
cctttaattt gattttcccg tttgtttcct cttcatgtcc agtgaaattt ttgttttgt    909 tttttcgg                                                            917
```

<210> SEQ ID NO 2
<211> LENGTH: 227
<212> TYPE: PRT
<213> ORGANISM: Phalaenopsis equestris

<400> SEQUENCE: 2

```
Met Gly Arg Gly Lys Ile Glu Ile Lys Lys Ile Glu Asn Pro Thr Asn
1               5                   10                  15

Arg Gln Val Thr Tyr Ser Lys Arg Arg Val Gly Ile Leu Lys Lys Ala
            20                  25                  30

Lys Glu Leu Thr Val Leu Cys Asp Ala Gln Val Ser Leu Ile Met Phe
        35                  40                  45

Ser Ser Thr Gly Lys Leu Ala Asp Tyr Cys Ser Pro Ser Thr Asp Ile
    50                  55                  60

Lys Gly Ile Tyr Glu Arg Tyr Gln Val Val Thr Gly Met Asp Leu Trp
65                  70                  75                  80

Asn Ala Gln Tyr Glu Arg Met Gln Asn Thr Leu Lys His Leu Asn Glu
                85                  90                  95

Ile Asn Gln Asn Leu Arg Lys Glu Ile Arg Arg Lys Gly Glu Glu
            100                 105                 110

Leu Glu Gly Met Asp Ile Lys Gln Leu Arg Gly Leu Glu Gln Thr Leu
        115                 120                 125

Glu Glu Ser Leu Arg Ile Val Arg His Arg Lys Tyr His Val Ile Ala
    130                 135                 140

Thr Gln Thr Asp Thr Tyr Lys Lys Leu Lys Ser Thr Arg Glu Thr
145                 150                 155                 160

Tyr Arg Ala Leu Ile His Glu Leu Asp Met Lys Glu Glu Asn Pro Asn
                165                 170                 175

Tyr Gly Phe Asn Val Glu Asn Gln Ser Arg Ile Tyr Glu Asn Ser Ile
            180                 185                 190

Pro Met Val Asn Glu Cys Pro Gln Met Phe Ser Phe Arg Val Val His
        195                 200                 205

Pro Asn Gln Pro Asn Leu Leu Gly Leu Gly Tyr Glu Ser His Asp Leu
    210                 215                 220

Ser Leu Ala
225
```

<210> SEQ ID NO 3
<211> LENGTH: 980
<212> TYPE: DNA
<213> ORGANISM: Phalaenopsis equestris
<220> FEATURE:
<221> NAME/KEY: CDS
<222> LOCATION: (196)..(864)

<400> SEQUENCE: 3

```
acgccacaac cctttggcca ttgcctgcta atggaaaccc agctgccact ttttccttcc    60
ccagccttat ataccttcag ttactctctt ctgcctccat ttttataagc atactttrcc   120
ccttttcttt cccatatcaa tctcaactcc ttcgcttctc ctgctgcttt gggaagcaga   180
gcaagaaaga gaacc atg ggg agg ggg aag atc gag ata aag aag att gag   231
              Met Gly Arg Gly Lys Ile Glu Ile Lys Lys Ile Glu
                1               5                   10
```

-continued

| | |
|---|---|
| aac cct aca aac agg cag gtt act tac tct aag agg agg gct ggg atc<br>Asn Pro Thr Asn Arg Gln Val Thr Tyr Ser Lys Arg Arg Ala Gly Ile<br>         15                       20                   25 | 279 |
| atg aaa aag gcg agc gag ctc acg gtt ctc tgt gat gct cag ctc tcc<br>Met Lys Lys Ala Ser Glu Leu Thr Val Leu Cys Asp Ala Gln Leu Ser<br> 30                      35                   40 | 327 |
| ctt gtt atg ttc tcc agc acc ggc aag ttc tcc gag tat tgt agt cct<br>Leu Val Met Phe Ser Ser Thr Gly Lys Phe Ser Glu Tyr Cys Ser Pro<br>45               50                   55                 60 | 375 |
| acc acc gat acc aag agt gta tat gat cgt tac cag cag gtg tcc ggc<br>Thr Thr Asp Thr Lys Ser Val Tyr Asp Arg Tyr Gln Gln Val Ser Gly<br>               65                   70                   75 | 423 |
| ata aat tta tgg agc gag cag tac gag aag atg cag aat acg ttg aat<br>Ile Asn Leu Trp Ser Glu Gln Tyr Glu Lys Met Gln Asn Thr Leu Asn<br>                  80                   85                  90 | 471 |
| cat ttg aag gag ata aac cac aac ttg agg agg gag ata agg cag agg<br>His Leu Lys Glu Ile Asn His Asn Leu Arg Arg Glu Ile Arg Gln Arg<br>          95                   100                 105 | 519 |
| atg ggc gag gat ctt gaa ggg cta gaa atc aaa gaa ctg cgt ggt ctt<br>Met Gly Glu Asp Leu Glu Gly Leu Glu Ile Lys Glu Leu Arg Gly Leu<br>       110                  115                 120 | 567 |
| gag caa aat atg gac gag gcc cta aag ctt gta agg aat cga aag tat<br>Glu Gln Asn Met Asp Glu Ala Leu Lys Leu Val Arg Asn Arg Lys Tyr<br>125               130                 135                 140 | 615 |
| cac gtc atc agc acc cag aca gat aca ttc aaa aaa aag ttg aaa aac<br>His Val Ile Ser Thr Gln Thr Asp Thr Phe Lys Lys Lys Leu Lys Asn<br>               145                 150                 155 | 663 |
| tct caa gaa acc cac agg aac tta ctc cgg gag ctg gaa act gag cac<br>Ser Gln Glu Thr His Arg Asn Leu Leu Arg Glu Leu Glu Thr Glu His<br>             160                 165                 170 | 711 |
| gcc gtc tac tac gtg gat gat gat cca aac aac tat gat ggc gcg ctt<br>Ala Val Tyr Tyr Val Asp Asp Asp Pro Asn Asn Tyr Asp Gly Ala Leu<br>               175                 180                 185 | 759 |
| gca ctt gga aat ggg gct tcc tac ttg tat tca ttt cgt acc caa cca<br>Ala Leu Gly Asn Gly Ala Ser Tyr Leu Tyr Ser Phe Arg Thr Gln Pro<br>       190                  195                 200 | 807 |
| agc cag ccg aac ctt cag gga gtt gga tat gtc cct cat gat cta cgt<br>Ser Gln Pro Asn Leu Gln Gly Val Gly Tyr Val Pro His Asp Leu Arg<br>205               210                 215                 220 | 855 |
| ctc gcc tga tcttttatta tctgcatgcc aactgcttaa ttatatctat<br>Leu Ala | 904 |
| gtatctgatg ttcttacgct tacaagtagg gtctagcact gcaatcgaat tcccgcggcc | 964 |
| gccagcggcc ggactc | 980 |

```
<210> SEQ ID NO 4
<211> LENGTH: 222
<212> TYPE: PRT
<213> ORGANISM: Phalaenopsis equestris

<400> SEQUENCE: 4
```

Met Gly Arg Gly Lys Ile Glu Ile Lys Lys Ile Glu Asn Pro Thr Asn
1                 5                     10                   15

Arg Gln Val Thr Tyr Ser Lys Arg Arg Ala Gly Ile Met Lys Lys Ala
                 20                   25                  30

Ser Glu Leu Thr Val Leu Cys Asp Ala Gln Leu Ser Leu Val Met Phe
                   35                   40                 45

Ser Ser Thr Gly Lys Phe Ser Glu Tyr Cys Ser Pro Thr Thr Asp Thr
 50                  55                   60

```
Lys Ser Val Tyr Asp Arg Tyr Gln Gln Val Ser Gly Ile Asn Leu Trp
 65                  70                  75                  80

Ser Glu Gln Tyr Glu Lys Met Gln Asn Thr Leu Asn His Leu Lys Glu
             85                   90                  95

Ile Asn His Asn Leu Arg Arg Glu Ile Arg Gln Arg Met Gly Glu Asp
            100                 105                 110

Leu Glu Gly Leu Glu Ile Lys Glu Leu Arg Gly Leu Glu Gln Asn Met
        115                 120                 125

Asp Glu Ala Leu Lys Leu Val Arg Asn Arg Lys Tyr His Val Ile Ser
    130                 135                 140

Thr Gln Thr Asp Thr Phe Lys Lys Lys Leu Lys Asn Ser Gln Glu Thr
145                 150                 155                 160

His Arg Asn Leu Leu Arg Glu Leu Glu Thr Glu His Ala Val Tyr Tyr
                165                 170                 175

Val Asp Asp Pro Asn Asn Tyr Asp Gly Ala Leu Ala Leu Gly Asn
            180                 185                 190

Gly Ala Ser Tyr Leu Tyr Ser Phe Arg Thr Gln Pro Ser Gln Pro Asn
            195                 200                 205

Leu Gln Gly Val Gly Tyr Val Pro His Asp Leu Arg Leu Ala
    210                 215                 220

<210> SEQ ID NO 5
<211> LENGTH: 1036
<212> TYPE: DNA
<213> ORGANISM: Phalaenopsis equestris
<220> FEATURE:
<221> NAME/KEY: CDS
<222> LOCATION: (216)..(887)

<400> SEQUENCE: 5
acgcggggca ctggcttcac tttcttccct gcggcaatgg ccaactattc ccggtaacta      60
tcgcttttgc gtttccagtt ctataaaagg aatccccgcc agagcttttt cttcttatag     120
agctttcttc ctcatctctc ccgttcgtca acatcactaa tcactgctgt ttcagtagac     180
tgggagagct aggagtggag aaaagagatt tgaag atg ggg agg ggg aag ata        233
                                       Met Gly Arg Gly Lys Ile
                                         1               5 gag att aag aag ata gag aat ccg act aat cgg cag gtg acc tac tcg       281
Glu Ile Lys Lys Ile Glu Asn Pro Thr Asn Arg Gln Val Thr Tyr Ser
         10                  15                  20 aag agg aga gct ggg att atg aag aag gcg agg gag atc act gtt ctc       329
Lys Arg Arg Ala Gly Ile Met Lys Lys Ala Arg Glu Ile Thr Val Leu
     25                  30                  35 tgc gat gct gag gtt tcg ctt atc atg ttc tcg agt act ggg aag ttt       377
Cys Asp Ala Glu Val Ser Leu Ile Met Phe Ser Ser Thr Gly Lys Phe
 40                  45                  50 tct gag tac tgt agc cct tcg acg gaa acg aag aag gtt ttt gaa cgc       425
Ser Glu Tyr Cys Ser Pro Ser Thr Glu Thr Lys Lys Val Phe Glu Arg
 55                  60                  65                  70 tac cag cag gta tct ggc att aac ttg tgg agc tcg cag tac gag aag       473
Tyr Gln Gln Val Ser Gly Ile Asn Leu Trp Ser Ser Gln Tyr Glu Lys
                 75                  80                  85 atg ctg aat acg ctt aac cat tcg aag gag atc aat cgc aat ctg agg       521
Met Leu Asn Thr Leu Asn His Ser Lys Glu Ile Asn Arg Asn Leu Arg
             90                  95                 100 agg gaa gta agg cag agg atg ggg gaa gat ctt gag gga ctg gat atc       569
Arg Glu Val Arg Gln Arg Met Gly Glu Asp Leu Glu Gly Leu Asp Ile
        105                 110                 115
```

```
aag gaa ctg cgc ggt ctt gag caa aac att gat gag gca ttg aag cta    617
Lys Glu Leu Arg Gly Leu Glu Gln Asn Ile Asp Glu Ala Leu Lys Leu
        120                 125                 130 gta cga aat aga aaa tat cat gta atc agt act caa acg gac acc tac    665
Val Arg Asn Arg Lys Tyr His Val Ile Ser Thr Gln Thr Asp Thr Tyr
135                 140                 145                 150 aag aag aag ttg aag aac tcc caa gaa aca cac cgg aac tta atg cac    713
Lys Lys Lys Leu Lys Asn Ser Gln Glu Thr His Arg Asn Leu Met His
                155                 160                 165 gaa ttg gaa atc gtt gag gac cac cca gtg tat ggg ttc cac gag gat    761
Glu Leu Glu Ile Val Glu Asp His Pro Val Tyr Gly Phe His Glu Asp
        170                 175                 180 tca agc aat tat gag ggt gtt ctt gct ctt gca aat gac ggg tct cac    809
Ser Ser Asn Tyr Glu Gly Val Leu Ala Leu Ala Asn Asp Gly Ser His
                185                 190                 195 atg tat gcc ttc cgg gtg caa ccc aac caa caa aat ctt caa gga acg    857
Met Tyr Ala Phe Arg Val Gln Pro Asn Gln Gln Asn Leu Gln Gly Thr
200                 205                 210 gga tat agc tct cac gat ctt cgc ctc gct tgatataatc gtgtaagtag      907
Gly Tyr Ser Ser His Asp Leu Arg Leu Ala
215                 220 tacaatcaca tatgcagtct tcattttatt gttcgcaaat tatgctctca gtagctggta   967
tctaatgtag aactaactac tgcaacttgc tcttatcttg ctatgtgtga ttctgtggta  1027
atgtggact                                                          1036

<210> SEQ ID NO 6
<211> LENGTH: 224
<212> TYPE: PRT
<213> ORGANISM: Phalaenopsis equestris

<400> SEQUENCE: 6

Met Gly Arg Gly Lys Ile Glu Ile Lys Lys Ile Glu Asn Pro Thr Asn
1               5                   10                  15

Arg Gln Val Thr Tyr Ser Lys Arg Arg Ala Gly Ile Met Lys Lys Ala
            20                  25                  30

Arg Glu Ile Thr Val Leu Cys Asp Ala Glu Val Ser Leu Ile Met Phe
        35                  40                  45

Ser Ser Thr Gly Lys Phe Ser Glu Tyr Cys Ser Pro Ser Thr Glu Thr
    50                  55                  60

Lys Lys Val Phe Glu Arg Tyr Gln Gln Val Ser Gly Ile Asn Leu Trp
65                  70                  75                  80

Ser Ser Gln Tyr Glu Lys Met Leu Asn Thr Leu Asn His Ser Lys Glu
                85                  90                  95

Ile Asn Arg Asn Leu Arg Arg Glu Val Arg Gln Arg Met Gly Glu Asp
            100                 105                 110

Leu Glu Gly Leu Asp Ile Lys Glu Leu Arg Gly Leu Glu Gln Asn Ile
        115                 120                 125

Asp Glu Ala Leu Lys Leu Val Arg Asn Arg Lys Tyr His Val Ile Ser
    130                 135                 140

Thr Gln Thr Asp Thr Tyr Lys Lys Lys Leu Lys Asn Ser Gln Glu Thr
145                 150                 155                 160

His Arg Asn Leu Met His Glu Leu Glu Ile Val Glu Asp His Pro Val
                165                 170                 175

Tyr Gly Phe His Glu Asp Ser Ser Asn Tyr Glu Gly Val Leu Ala Leu
            180                 185                 190
```

```
Ala Asn Asp Gly Ser His Met Tyr Ala Phe Arg Val Gln Pro Asn Gln
        195                 200                 205
Gln Asn Leu Gln Gly Thr Gly Tyr Ser Ser His Asp Leu Arg Leu Ala
    210                 215                 220

<210> SEQ ID NO 7
<211> LENGTH: 898
<212> TYPE: DNA
<213> ORGANISM: Phalaenopsis equestris
<220> FEATURE:
<221> NAME/KEY: CDS
<222> LOCATION: (123)..(782)

<400> SEQUENCE: 7
tcgcaacacg aggcgctgtc ggcgagtcgg gttgtttggg aatgcagccc taatcgggcg      60
gtaaattccg tccaaggcta aatacgggcg agagaccgat agcgaacaag taccgcgagg     120 ga atg ggg aga ggg aag ata gag ata aag aag ata gag aat cca aca        167
   Met Gly Arg Gly Lys Ile Glu Ile Lys Lys Ile Glu Asn Pro Thr
   1               5                   10                  15 agc agg caa gta acg tat tca aag agg cga ctt ggg atc atg aag aag      215
Ser Arg Gln Val Thr Tyr Ser Lys Arg Arg Leu Gly Ile Met Lys Lys
                20                  25                  30 gca gag gaa ctc aca gtg ctc tgc gac gct caa ctc tca ctc atc atc      263
Ala Glu Glu Leu Thr Val Leu Cys Asp Ala Gln Leu Ser Leu Ile Ile
            35                  40                  45 ttc tca agc tcc ggc aag tta gct gat ttc tgc agc cct tcc aca gac      311
Phe Ser Ser Ser Gly Lys Leu Ala Asp Phe Cys Ser Pro Ser Thr Asp
        50                  55                  60 gtt aaa gat ata gtt gag agg tac caa aat gtt acc gga att gat ata      359
Val Lys Asp Ile Val Glu Arg Tyr Gln Asn Val Thr Gly Ile Asp Ile
    65                  70                  75 tgg gat gcg caa tat cag agg atg cag aac act ctg agg aat ctc agg      407
Trp Asp Ala Gln Tyr Gln Arg Met Gln Asn Thr Leu Arg Asn Leu Arg
80                  85                  90                  95 gag att aat cgt aat ctt cag aag gag ata aga cag agg aag ggg gag      455
Glu Ile Asn Arg Asn Leu Gln Lys Glu Ile Arg Gln Arg Lys Gly Glu
                100                 105                 110 aat ctg gaa ggg ttg ggc gtt aaa gag ctg cgc ggt ctt gag caa aaa      503
Asn Leu Glu Gly Leu Gly Val Lys Glu Leu Arg Gly Leu Glu Gln Lys
            115                 120                 125 ttg gag gag tcg gtt aag att gtt cgg cag aga aag tat cat gtg atc      551
Leu Glu Glu Ser Val Lys Ile Val Arg Gln Arg Lys Tyr His Val Ile
        130                 135                 140 gct acg caa aca gac act tgc agg aaa aag ctc aaa agc agc aga caa      599
Ala Thr Gln Thr Asp Thr Cys Arg Lys Lys Leu Lys Ser Ser Arg Gln
    145                 150                 155 ata tac aga gcc cta acg cat gaa ctg cag aag ctg gac gaa gag aat      647
Ile Tyr Arg Ala Leu Thr His Glu Leu Gln Lys Leu Asp Glu Glu Asn
160                 165                 170                 175 caa ccg tgc agt ttt ctc gta gaa gat cta agc tgc atc tat gac agc      695
Gln Pro Cys Ser Phe Leu Val Glu Asp Leu Ser Cys Ile Tyr Asp Ser
                180                 185                 190 tca atc tca atg gca aat cgg ctg cac cgg agt gag cca aat gtg cag      743
Ser Ile Ser Met Ala Asn Arg Leu His Arg Ser Glu Pro Asn Val Gln
            195                 200                 205 aaa gta gtt cgt gag tgt cat gag ttt ggc ttt gat tga cctgcaattt       792
Lys Val Val Arg Glu Cys His Glu Phe Gly Phe Asp
        210                 215
```

```
tctattactt tgtgttacaa tgtggatttg ttttcatggc ttaacatcat aggattgtat    852
aaactatttt tttgtgtgca atgtttaagt tctgatcttg atatcc                   898
```

<210> SEQ ID NO 8
<211> LENGTH: 219
<212> TYPE: PRT
<213> ORGANISM: Phalaenopsis equestris

<400> SEQUENCE: 8

```
Met Gly Arg Gly Lys Ile Glu Ile Lys Lys Ile Glu Asn Pro Thr Ser
1               5                   10                  15

Arg Gln Val Thr Tyr Ser Lys Arg Arg Leu Gly Ile Met Lys Lys Ala
            20                  25                  30

Glu Glu Leu Thr Val Leu Cys Asp Ala Gln Leu Ser Leu Ile Ile Phe
        35                  40                  45

Ser Ser Ser Gly Lys Leu Ala Asp Phe Cys Ser Pro Ser Thr Asp Val
    50                  55                  60

Lys Asp Ile Val Glu Arg Tyr Gln Asn Val Thr Gly Ile Asp Ile Trp
65                  70                  75                  80

Asp Ala Gln Tyr Gln Arg Met Gln Asn Thr Leu Arg Asn Leu Arg Glu
                85                  90                  95

Ile Asn Arg Asn Leu Gln Lys Glu Ile Arg Gln Arg Lys Gly Glu Asn
            100                 105                 110

Leu Glu Gly Leu Gly Val Lys Glu Leu Arg Gly Leu Glu Gln Lys Leu
        115                 120                 125

Glu Glu Ser Val Lys Ile Val Arg Gln Arg Lys Tyr His Val Ile Ala
    130                 135                 140

Thr Gln Thr Asp Thr Cys Arg Lys Lys Leu Lys Ser Ser Arg Gln Ile
145                 150                 155                 160

Tyr Arg Ala Leu Thr His Glu Leu Gln Lys Leu Asp Glu Glu Asn Gln
                165                 170                 175

Pro Cys Ser Phe Leu Val Glu Asp Leu Ser Cys Ile Tyr Asp Ser Ser
            180                 185                 190

Ile Ser Met Ala Asn Arg Leu His Arg Ser Glu Pro Asn Val Gln Lys
        195                 200                 205

Val Val Arg Glu Cys His Glu Phe Gly Phe Asp
    210                 215
```

<210> SEQ ID NO 9
<211> LENGTH: 25
<212> TYPE: DNA
<213> ORGANISM: Artificial
<220> FEATURE:
<223> OTHER INFORMATION: PeMADS2 specific primer

<400> SEQUENCE: 9

```
tctctctgaa tagatccccc atctc                                           25
```

<210> SEQ ID NO 10
<211> LENGTH: 25
<212> TYPE: DNA
<213> ORGANISM: Artificial
<220> FEATURE:
<223> OTHER INFORMATION: PeMADS3 specific primer

<400> SEQUENCE: 10

```
gcagtgctag accctacttg taagc                                           25
```

<210> SEQ ID NO 11
<211> LENGTH: 27
<212> TYPE: DNA
<213> ORGANISM: Artificial
<220> FEATURE:
<223> OTHER INFORMATION: PeMADS4 specific primer

<400> SEQUENCE: 11
gctatatccc gttccttgaa gattttg                                27

<210> SEQ ID NO 12
<211> LENGTH: 25
<212> TYPE: DNA
<213> ORGANISM: Artificial
<220> FEATURE:
<223> OTHER INFORMATION: PeMADS5 specific primer

<400> SEQUENCE: 12
tcctatgatg ttaagccatg aaaac                                  25

<210> SEQ ID NO 13
<211> LENGTH: 21
<212> TYPE: DNA
<213> ORGANISM: Artificial
<220> FEATURE:
<223> OTHER INFORMATION: nested PeMADS2-specific primer

<400> SEQUENCE: 13
tgattcggat gaacaaccct a                                      21

<210> SEQ ID NO 14
<211> LENGTH: 21
<212> TYPE: DNA
<213> ORGANISM: Artificial
<220> FEATURE:
<223> OTHER INFORMATION: nested PeMADS3-specific primer

<400> SEQUENCE: 14
aggaagcccc atttccaagt g                                      21

<210> SEQ ID NO 15
<211> LENGTH: 21
<212> TYPE: DNA
<213> ORGANISM: Artificial
<220> FEATURE:
<223> OTHER INFORMATION: nested PeMADS4-specific primer

<400> SEQUENCE: 15
gtgcattaag ttccggtgtg t                                      21

<210> SEQ ID NO 16
<211> LENGTH: 21
<212> TYPE: DNA
<213> ORGANISM: Artificial
<220> FEATURE:
<223> OTHER INFORMATION: nested PeMADS5-specific primer

<400> SEQUENCE: 16
tgcacatttg gctcactccg g                                      21

<210> SEQ ID NO 17
<211> LENGTH: 18
<212> TYPE: DNA
<213> ORGANISM: Artificial
<220> FEATURE:
<223> OTHER INFORMATION: PeMADS2-specific internal forward primer

<400> SEQUENCE: 17
gaaacttacc gcgctcta					18

<210> SEQ ID NO 18
<211> LENGTH: 25
<212> TYPE: DNA
<213> ORGANISM: Artificial
<220> FEATURE:
<223> OTHER INFORMATION: PeMADS2-specific internal reverse primer

<400> SEQUENCE: 18
tctctctgaa tagatccccc atctc				25

<210> SEQ ID NO 19
<211> LENGTH: 18
<212> TYPE: DNA
<213> ORGANISM: Artificial
<220> FEATURE:
<223> OTHER INFORMATION: PeMADS3-specific internal forward primer

<400> SEQUENCE: 19
ctctcaagaa acccacag					18

<210> SEQ ID NO 20
<211> LENGTH: 25
<212> TYPE: DNA
<213> ORGANISM: Artificial
<220> FEATURE:
<223> OTHER INFORMATION: PeMADS3-specific internal recerse primer

<400> SEQUENCE: 20
gcagtgctag accctacttg taagc				25

<210> SEQ ID NO 21
<211> LENGTH: 18
<212> TYPE: DNA
<213> ORGANISM: Artificial
<220> FEATURE:
<223> OTHER INFORMATION: PeMADS4-specific internal forward primer

<400> SEQUENCE: 21
gaggaccacc cagtgtat					18

<210> SEQ ID NO 22
<211> LENGTH: 19
<212> TYPE: DNA
<213> ORGANISM: Artificial
<220> FEATURE:
<223> OTHER INFORMATION: PeMADS4-specific internal reverse primer

<400> SEQUENCE: 22
cacagaatca cacatagca					19

<210> SEQ ID NO 23
<211> LENGTH: 18
<212> TYPE: DNA
<213> ORGANISM: Artificial
<220> FEATURE:
<223> OTHER INFORMATION: PeMADS5-specific internal forward primer

<400> SEQUENCE: 23
caaacagaca cttgcagg					18

```
<210> SEQ ID NO 24
<211> LENGTH: 25
<212> TYPE: DNA
<213> ORGANISM: Artificial
<220> FEATURE:
<223> OTHER INFORMATION: PeMADS5-specific internal reverse primer

<400> SEQUENCE: 24
tcctatgatg ttaagccatg aaaac                                             25
```